(12) United States Patent
Ekman et al.

(10) Patent No.: US 9,339,609 B2
(45) Date of Patent: May 17, 2016

(54) INJECTION DEVICE

(75) Inventors: Matthew Ekman, Cheshire (GB); Christopher James Smith, Cheshire (GB); Troy Baker, St. Asaph (GB); Graham Wilson, Flintshire (GB); Gareth Roberts, Wrexham (GB); John Slemmen, Mereyside (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 156 days.

(21) Appl. No.: 14/240,805

(22) PCT Filed: Sep. 11, 2012

(86) PCT No.: PCT/EP2012/067689
§ 371 (c)(1),
(2), (4) Date: Feb. 25, 2014

(87) PCT Pub. No.: WO2013/037744
PCT Pub. Date: Mar. 21, 2013

(65) Prior Publication Data
US 2014/0200518 A1     Jul. 17, 2014

(30) Foreign Application Priority Data
Sep. 13, 2011     (EP) .................................... 11181038

(51) Int. Cl.
*A61M 5/32*          (2006.01)
(52) U.S. Cl.
CPC .............. *A61M 5/3204* (2013.01); *A61M 5/326* (2013.01); *A61M 5/3202* (2013.01); *A61M 2005/3263* (2013.01); *A61M 2005/3267* (2013.01); *A61M 2205/586* (2013.01)

(58) Field of Classification Search
CPC ............. A61M 2005/3263; A61M 2005/3267; A61M 2205/586; A61M 5/3202; A61M 5/3204; A61M 5/326
See application file for complete search history.

(56) References Cited

U.S. PATENT DOCUMENTS 6,210,369 B1     4/2001   Wilmot et al.

FOREIGN PATENT DOCUMENTS

| EP | 0467173 | 1/1992 |
|---|---|---|
| WO | 03/013632 | 2/2003 |
| WO | 2010/121289 | 10/2010 |
| WO | 2011/048223 | 4/2011 |

OTHER PUBLICATIONS

International Search Report for Int. App No. PCT/EP2012/067689, completed Dec. 17, 2012.

*Primary Examiner* — Imani Hayman
(74) *Attorney, Agent, or Firm* — Fish & Richardson P.C.

(57) ABSTRACT

An injection device comprises a pre-filled syringe and a safety mechanism for providing needle safety for an injection needle of the syringe. The syringe comprises a barrel containing the liquid and a stopper disposed within the barrel. The needle is attached to a distal end of the barrel. The safety mechanism comprises a substantially cylindrical housing adapted to contain the syringe, a plunger to expel the liquid through the injection needle, and an energizable biasing member arranged between the housing and the syringe. The energized biasing member is capable of biasing the syringe with respect to the housing in a proximal direction and a retaining mechanism for retaining the syringe with respect to the housing in a first retracted position in an advanced position and in a second retracted position.

13 Claims, 9 Drawing Sheets

INJECTION DEVICE

CROSS REFERENCE TO RELATED APPLICATIONS

The present application is a U.S. National Phase Application pursuant to 35 U.S.C. §371 of International Application No. PCT/EP2012/067689 filed Sep. 11, 2012, which claims priority to European Patent Application No. 11181038.8 filed Sep. 13, 2011. The entire disclosure contents of these applications are herewith incorporated by reference into the present application.

TECHNICAL FIELD

The present invention relates to safety devices that provide needle safety and more particularly to safety devices for pre-filled syringes. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle, for example syringe of WO 2010/121289 A1 or EP 0 467 173 A1 or automatic injector of U.S. Pat. No. 6,210,369 B1.

A different type of safety devices known in the state of the art solve the object of providing needle safety by arranging the pre-filled syringe movable relative to a body, whereas the pre-filled syringe is retracted into the body after the injection.

SUMMARY

It is an object of the invention to provide an improved injection device comprising a pre-filled syringe that is safe to handle and in particular prevents accidental needle stick injuries.

The object is achieved by an injection device according to claims 1 and 4.

Preferred embodiments of the invention are given in the dependent claims.

In the context of this specification, the terms distal and proximal are defined from the point of view of a person performing an injection. Consequently, a distal direction refers to a direction pointing towards the body of patient receiving an injection and a distal end defines an end of an element that is directed towards the body of the patient. Respectively, the proximal end of an element or the proximal direction is directed away from the body of the patient receiving the injection and opposite to the distal end or distal direction.

According to an embodiment of the invention, an injection device for administering a liquid comprises a pre-filled syringe and a safety mechanism for providing needle safety for an injection needle of the pre-filled syringe. The pre-filled syringe comprises a barrel containing the liquid,
a stopper translatably disposed within the barrel,
the injection needle attached to a distal end of the barrel.

The safety mechanism comprises a substantially cylindrical housing adapted to contain the pre-filled syringe,
a plunger connectable to the stopper of the pre-filled syringe and adapted to be translated in a distal direction to expel liquid through the injection needle,
an energizable biasing means arranged between the housing and the pre-filled syringe, wherein the energized biasing means is capable of biasing the pre-filled syringe with respect to the housing in a proximal direction and
a retaining mechanism for retaining the pre-filled syringe with respect to the housing in a first retracted position, in an advanced position and in a second retracted position.

The injection needle is covered by the housing in the first and second retracted positions and projects distally from the housing in the advanced position. The biasing means is arranged in a non-energized state when the pre-filled syringe is in the first retracted position. The biasing means is adapted to be energized upon translation of the pre-filled syringe from the first retracted position to the advanced position so as to bias the syringe from the advanced position towards the second retracted position.

The injection device is designed as a single use device that minimizes the risk of an accidental needle stick injury after the injection is performed. In particular, infections caused by inadvertent contact with a used injection needle may be avoided.

The biasing means of the injection device is arranged to withdraw the injection needle into the housing after the injection. The biasing means is disposed in a non-energized and relaxed state before use and is energized and stressed just before the injection is carried out. Arrangement of the biasing means in the relaxed state before use reduces material fatigue so as to extend the lifespan of injection device. Moreover, the biasing means may be made from alternative materials that would not resist being stored in a stressed state for extended periods, like, for example, plastic materials. As these materials are typically inexpensive, the production costs for the injection device are significantly lowered.

The injection device comprises only few parts further reducing the production costs. The injection device is thus well suited to be used as a single use device as it may be manufactured in large quantities at low costs.

Preferably, a boot that is detachably connected to the distal end of the barrel covers the injection needle before an injection and retains the injection needle in a sterile environment before use. Additionally, the boot provides a means for manually translating the pre-filled syringe from the first retracted position to the advanced position. The user of the injection device simply pulls the boot in the distal direction before the injection is performed, whereby the pre-filled syringe is advanced towards the advanced position and the biasing means is charged and energized. The boot may be removed to uncover the injection needle by continuous application of a force in the distal direction after the pre-filled syringe reached the advanced position.

According to a possible embodiment of the invention, the retaining mechanism comprises at least one latch arm that is arranged on the housing so as to pivot with respect to the housing about a pivot point. The pivoting movement of the latch arm allows for a frictional engagement and disengagement of the barrel or a collar of the syringe so as to temporarily mount the pre-filled syringe in at least the first retracted position and in the advanced position.

The at least one latch arm of the retaining means is arranged to interact with a guide rail of the plunger. The guide rail travels along a guide track formed to an outer surface of the housing when the plunger is depressed into the barrel to expel the liquid medicament contained therein through the injection needle. When the plunger is bottoms out within the barrel, the guide rail abuts against the latch arm to resiliently deflect the latch arm radially outwards. The latch arm pivots about the pivot point, whereby the syringe that is retained in the advanced position is disengaged and released when the plunger is substantially depressed into the barrel.

According to another embodiment of the invention, an injection device for administering a liquid comprises a pre-filled syringe and a safety mechanism for providing needle safety for an injection needle of the pre-filled syringe. The pre-filled syringe comprises
a barrel containing the liquid,
a stopper translatably disposed within the barrel and
the injection needle attached to a distal end of the barrel.
The safety mechanism comprises
a substantially cylindrical housing adapted to contain the pre-filled syringe,
a plunger connectable to the stopper of the pre-filled syringe and adapted to be translated in a distal direction to expel the liquid through the injection needle,
a needle shield translatably disposed with respect to the housing,
an energizable biasing means arranged between the housing and the needle shield, wherein the energized biasing means is capable of biasing the needle shield with respect to the housing in the distal direction,
an activation element adapted to be translated with respect to the housing from a proximal position to a distal position and
a retaining mechanism for retaining the needle shield with respect to the housing in a first position and in a second position.

The injection needle projects distally from the needle shield in the first position and is covered by the needle shield in the second position. The biasing means is arranged in a non-energized state when the activation element is in the proximal position. The biasing means is adapted to be energized upon translation of the activation element from the proximal position to the distal position so as to bias the needle shield from the first position towards the second position.

The biasing means of the injection device is arranged to advance the needle shield to cover the injection needle after the injection. The biasing means is disposed in a non-energized and relaxed state before use and is energized and stressed just before the injection is carried out. Arrangement of the biasing means in the relaxed state before use reduces material fatigue so as to extend the lifespan of injection device. Moreover, the biasing means may be made from alternative materials that would not resist being stored in a stressed state for extended periods, like, for example, plastic materials. As these materials are typically inexpensive, the production costs for the injection device may be significantly lowered.

Alternatively, the biasing means may be arranged as a compression spring made from a metal.

Preferably, a cover element is detachably connected to the distal end of the housing. The cover element surrounds the injection needle before an injection and protects from inadvertent contact therewith. Additionally, the cover element is releasably coupled to the activation element so as to provide a means for translating the activation element from the proximal position to the distal position whereby the biasing means is energized and tensioned.

A boot may be arranged to cover the injection needle before use. The boot retains the injection needle in a sterile environment so as to minimize the risk of infections. Advantageously, the boot is integrated to the cover element.

The cover element may comprise at least one clamp arm that is adapted to latch to the activation element to releasably couple the cover element to the activation element. The cover element is removed from housing by simply pulling the cover element in the distal direction, whereby the activation element is translated from the proximal position to the distal position so as to charge and energize the biasing means.

The housing may comprise at least one ramped first protrusion that is arranged so as to allow for a translation of the activation element from the proximal position to the distal position. The biasing means arranged between the needle shield and the activation element is fully compressed and thus energized when needle shield is in the first position and the activation element is in the distal position. The activation element is firmly secured in the distal position by the first protrusion and provides a bearing that allows for a translation of the needle shield from the first to second position under the load of the biasing means upon release.

According to another possible embodiment, a retaining mechanism comprises at least one ramped first clip and at least one second clip arranged on the needle shield and adapted to engage the housing to retain the needle shield in the first and second positions. The first clip is adapted to releasably retain the needle shield in the first position and the second clip is adapted to firmly retain and lock the needle shield in the second position so as to prevent an inadvertent exposure of the injection needle after the injection. The needle shield may be designed to irreversibly lock the needle shield to the advanced second position so as to prevent a re-usage of the injection device. This in particular minimizes the risk of infections with diseases that are transmitted through contact with bodily fluids.

The retaining mechanism may further comprise a release element adapted to release the needle shield retained in the first position so that the needle shield may be translated distally under the load of the biasing means to cover the injection needle after the injection. The release element is adapted to be translated with respect to the housing in the distal direction, wherein the distal translation of the release element engages and abuts against the ramped surface of the first clip. The first clip is resiliently deflected so as to release the needle shield from being retained in the first position.

Preferably, the release element may be coupled to the movement of the plunger. The release element may project from the housing in the proximal direction so that a thumb rest arranged on the distal end of the plunger may abut against the release element when the plunger is substantially depressed into the barrel. The release element is translated distally by pushing the plunger distally and depressing the plunger completely into the barrel to substantially expel the remaining medicament contained in the pre-filled syringe. The needle shield is thus released at the end of the injection stroke delivering the medicament beneath the skin of the patient.

The release element may further comprise a first shoulder and the housing may further comprise a corresponding second shoulder. The shoulders operate as guidance and stopper. The first shoulder is arranged to abut against the second shoulder to limit the distal translation of the release element.

According to another possible embodiment of the invention, the biasing means is made from a plastic material with a shape memory like rubber or an elastomer. Plastic materials are inexpensive and thus help to reduce manufacturing costs of the injection device.

Preferably, the energizable biasing means is made from compressible and resilient foam material like polyurethane that is compressed and thus energized immediately before an injection is performed.

The injection device is particularly suited for self-administered injections. Thus, the term patient or user may refer to one and the same person.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

Corresponding parts are marked with the same reference symbols in all figures.

DETAILED DESCRIPTION

Figure 1A:
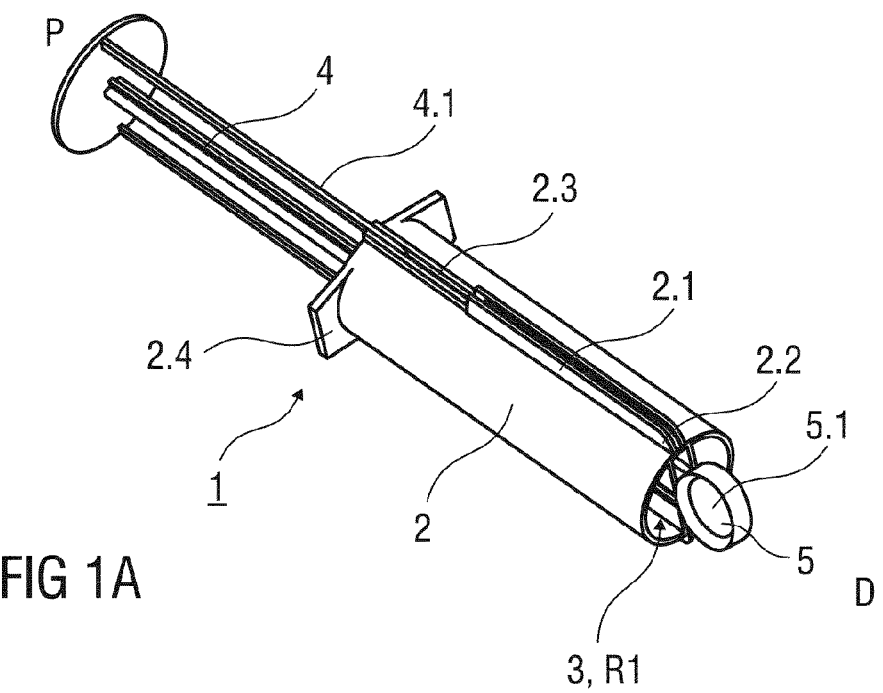
FIG. 1A to 1D show perspective views of a first embodiment of an injection device.

FIG. 1A to 1D show perspective views of an injection device 1 according to a first embodiment of the invention. The injection device 1 comprises a substantially cylindrical housing 2 containing a pre-filled syringe 3 translatably disposed therein. A plunger 4 projects proximally from the pre-filled syringe 3 and the housing 2. The plunger 4 is arranged to be depressed into a barrel 3.1 of the pre-filled syringe 3 to expel a medication contained therein through an injection needle 3.2 attached to a distal end of the pre-filled syringe 3.

Two pivotable latch arms 2.1 project from opposite sides of a lateral wall of the housing 2 and extend substantially parallel thereto. Each latch arm 2.1 is arranged to pivot about a pivot point 2.2 when a guide rail 4.1 integral with the plunger 4 and travelling along a guide track 2.3 during the drug delivery stage reaches a distal end stop. The latch arm 2.1 retains the pre-filled syringe 3 in position with respect to the housing 2.

A flange 2.4 is formed to a proximal end of the housing 2 that projects in a radial direction to support the fingers of user during an injection.

FIG. 1A shows the injection device 1 in a packaged state as it would be delivered to an end-user. The pre-filled syringe 3 is retained within the housing 2 in a first retracted position R1 so as to surround the injection needle 3.2 allowing for a safe transport of the injection device 1.

Additionally, an elongated boot 5 is frictionally affixed to a nozzle 3.2 formed to the distal end of the barrel 3.1 of the pre-filled syringe 3. The boot 5 covers the injection needle 3.2 in the packaged state and comprises gripping means 5.1 that project from the housing 2 in the distal direction D. The gripping means 5.1 are adapted to be gripped and pulled by a user to translate the pre-filled syringe 3 from the first retracted position R1 to an advanced position A shown in FIG. 1B.

Figure 1B:
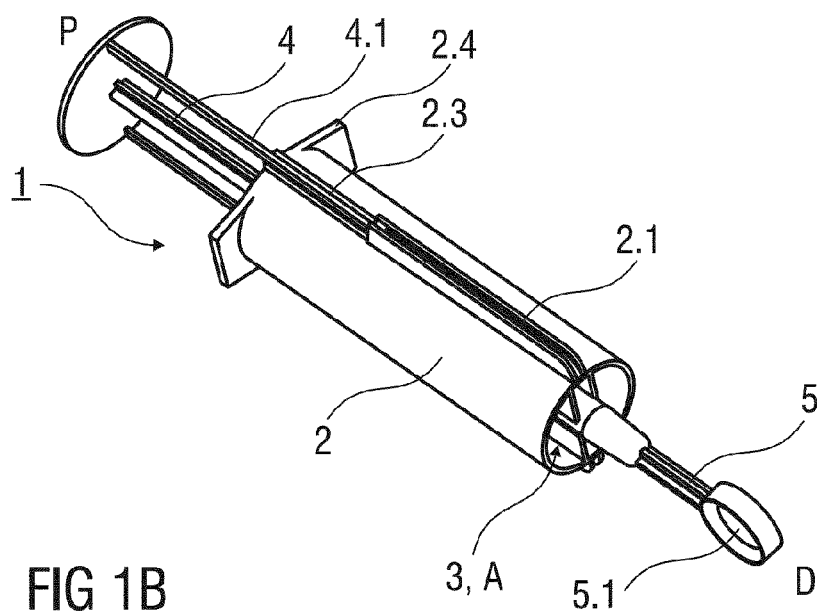

FIG. 1B shows the injection device 1 with the pre-filled syringe 3 in the advanced position A. As will be described in herein below in more detail, advancing the pre-filled syringe 3 from the first retracted position R1 to the advanced position A relates to charging and energizing a biasing means 6 disposed between the pre-filled syringe 3 and the housing 2. The energized biasing means 6 is capable of retracting the pre-filled syringe 3 from the advanced position A into the housing 2 after the injection is completed to prevent accidental needle stick injuries with used injection needles 3.2.

Figure 1C:
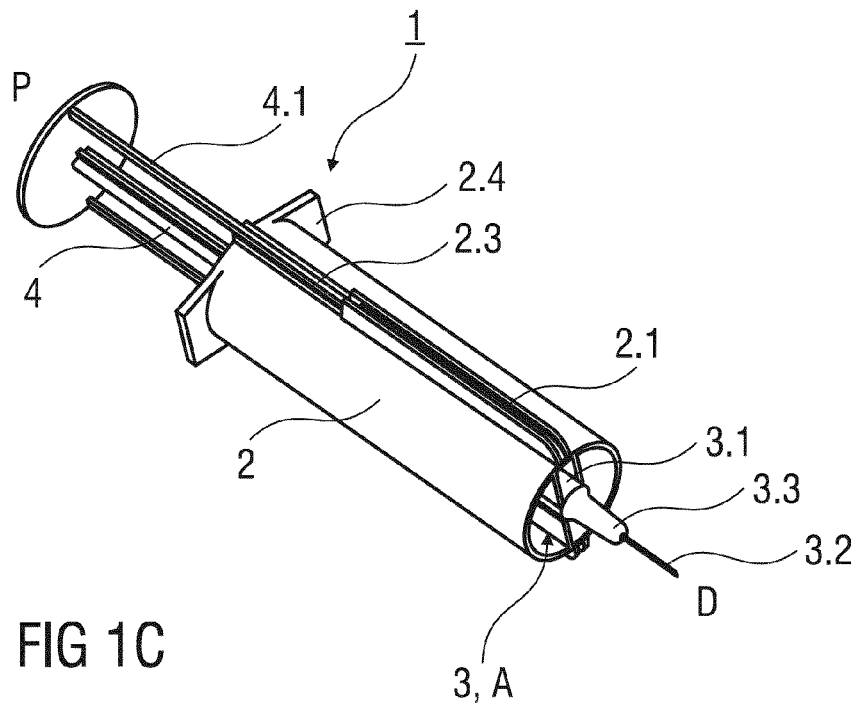

As illustrated in FIG. 1C, the boot 5 is pulled off the nozzle 3.3 to uncover the injection needle 3.2 projecting from the distal end of the housing 2. The injection device 1 is now prepared for an injection delivering the medicament contained in the pre-filled syringe 3 beneath the skin of a patient.

Figure 1D:
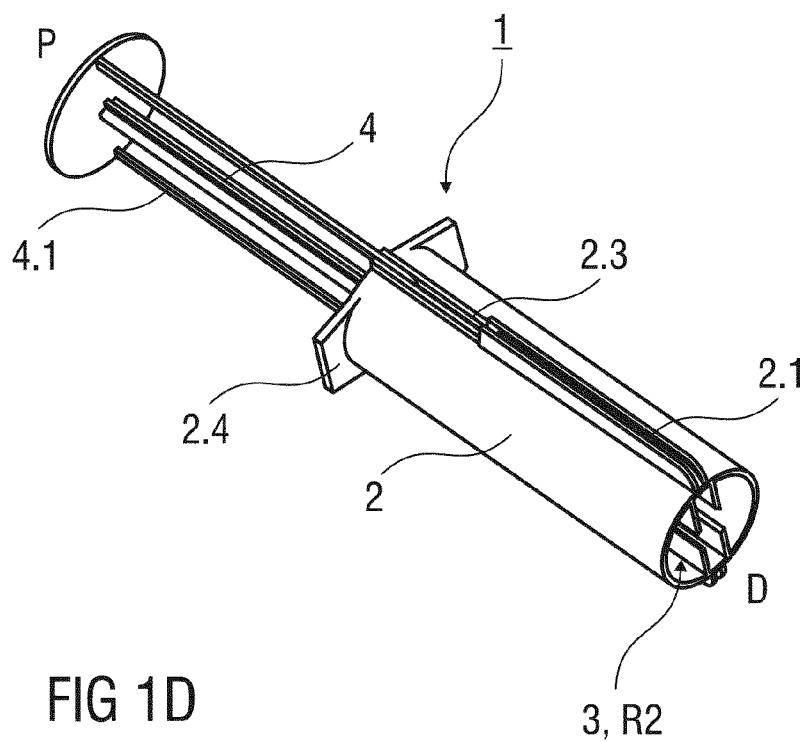

FIG. 1D shows the injection device 1 according to the first embodiment of the invention in a post drug delivery state. The empty syringe 3 is retracted within the housing 2 in a second retracted position R2 to cover the injection needle 3.2 so as to provide needle safety.

Figure 2:
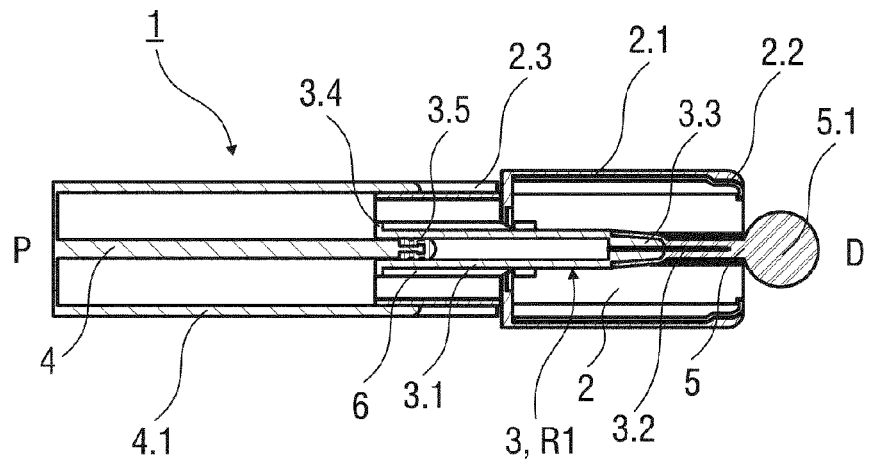
FIG. 2 shows a sectional view of the injection device according to the first embodiment of the invention in a packaged state.

FIG. 2 shows a sectional view of the injection device 1 according to the first embodiment of the invention in its packaged state. The pre-filled syringe 3 is firmly but releasably retained in the first retracted position R1 by the latch arms 2.1 that protrude into the housing 2 to frictionally engage the barrel 3.1 of the pre-filled syringe 3. The biasing means 6 disposed between a proximal collar 3.4 of the pre-filled syringe 3 and the housing 2 is in a non-tensioned state. Arrangement of the biasing means 6 in the relaxed state during transport and storage avoids material fatigue and thus extends the life time of the injection device 1.

The biasing means 6 of the first embodiment is made from a resiliently deformable plastic material, in particular a compressible foam material like polyurethane. The foam may be compressed to energize the biasing means 6 so as to allow for a retraction of the pre-filled syringe 3 into the housing after injection of the medicament.

A stopper 3.5 is translatably arranged within the barrel 3.1 and provides a fluid tight seal for the proximal end thereof. The stopper 3.5 is connected to the plunger 4 and travels within the barrel 3.1 in the distal direction D when the plunger 4 is depressed into the barrel 3.1 to expel the liquid medicament disposed therein through the injection needle 3.2.

Figure 3:
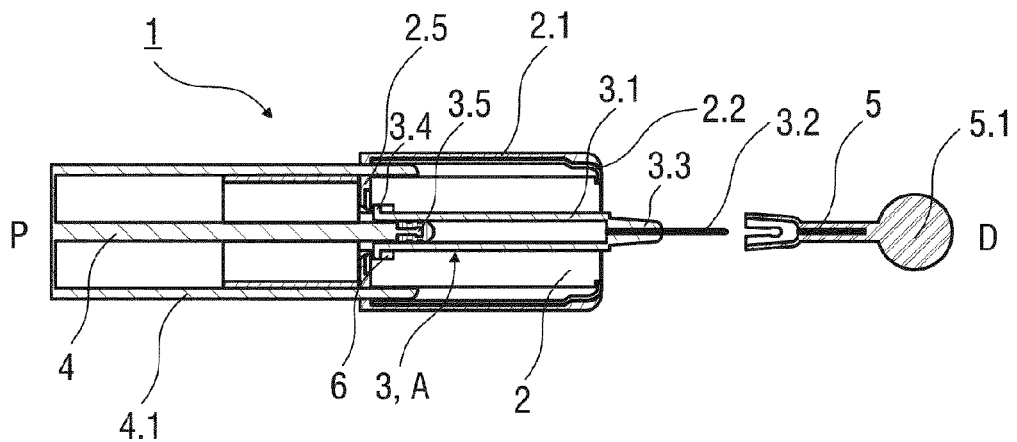
FIG. 3 illustrates energizing of a biasing means of the injection device according to the first embodiment of the invention in a sectional view.

FIG. 3 illustrates the energizing and charging of the biasing means 6 before the drug delivery stage. The pre-filled syringe 3 is advanced in the distal direction D by pulling the boot 5 projecting distally from the housing 2 of the injection device 1. The pre-filled syringe 3 is moved from the first retracted position R1 to the advanced position A against the resistance of the biasing means 6. The biasing means 6 is compressed and charged when the pre-filled syringe 3 is retained in the advanced position A by the inward projections 2.5 projecting from the latch arms 2.1 inwards into the housing 2 and latching to the collar 3.4 of the pre-filled syringe 3.

The ramped engagement of the inward projections 2.5 with the collar 3.4 cause the latch arms 2.1 to pivot about the pivot point 2.2 when the pre-filled syringe 3 is translated from the first retracted position R1 in the distal direction D. The inward projections 2.5 overcome the collar 3.4 and abut against the collar 3.4 in the distal direction D to releasably retain the pre-filled syringe 3 in the advanced position A.

Figure 4:
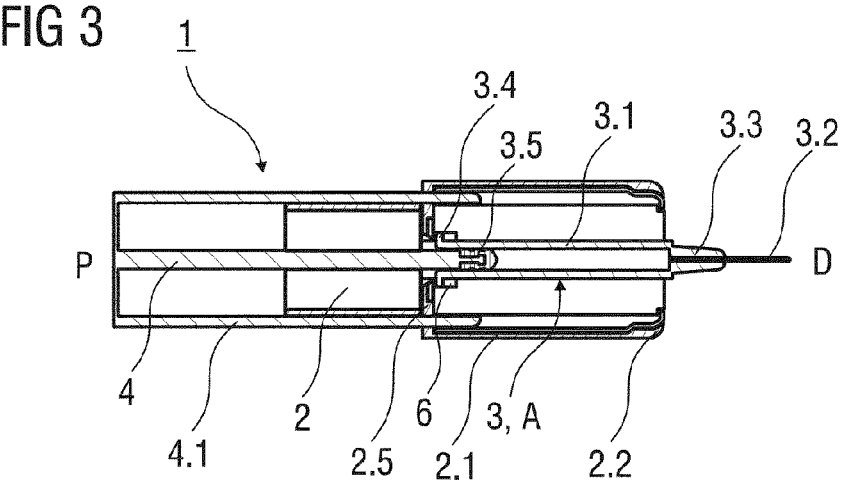
FIG. 4 shows a sectional view of the injection device according to the first embodiment of the invention before drug delivery.

FIG. 4 shows the injection device 1 prepared to deliver the medicament contained in the pre-filled syringe 3 to a patient. The boot 5 has been removed from the nozzle 3.3 exposing the injection needle 3.2 projecting distally from the housing 2. The biasing means 6 is fully compressed and biases the pre-filled syringe 3 with respect to the housing 2 in the proximal direction P. A proximal movement of the pre-filled syringe 3 is prevented by the inward projections 2.5 of the latch arms 2.1 abutting against the collar 3.4 of the pre-filled syringe 3 in the distal direction D.

Figure 5:
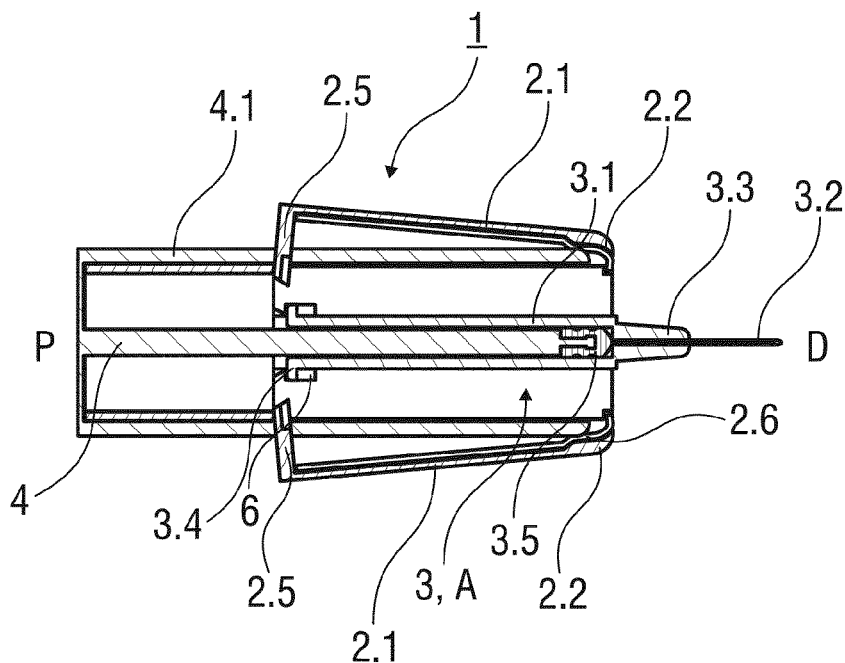
FIG. 5 shows a sectional view of the injection device according to the first embodiment of the invention after drug delivery.

FIG. 5 shows a sectional view of the injection device 1 at the end of an injection stroke expelling the medicament through the injection needle 3.2. The plunger 4 is fully depressed into the syringe 3 and the stopper 3.5 has bottomed out in the barrel 3.1. The guide rail 4.1 abuts against a ramp 2.6 arranged at a distal end of the latch arms 2.1 close to the pivot point 2.2 so as to resiliently deflect the latch arm 2.1 radial outwards. The inward projections 2.5 disengage the collar 3.4 releasing the syringe 3 from being retained in the advanced position A. The syringe 3 may now be translated under the load of the biasing means 6 from the advanced position A to a needle safe second retracted position R2 shown in FIG. 6.

Figure 6:
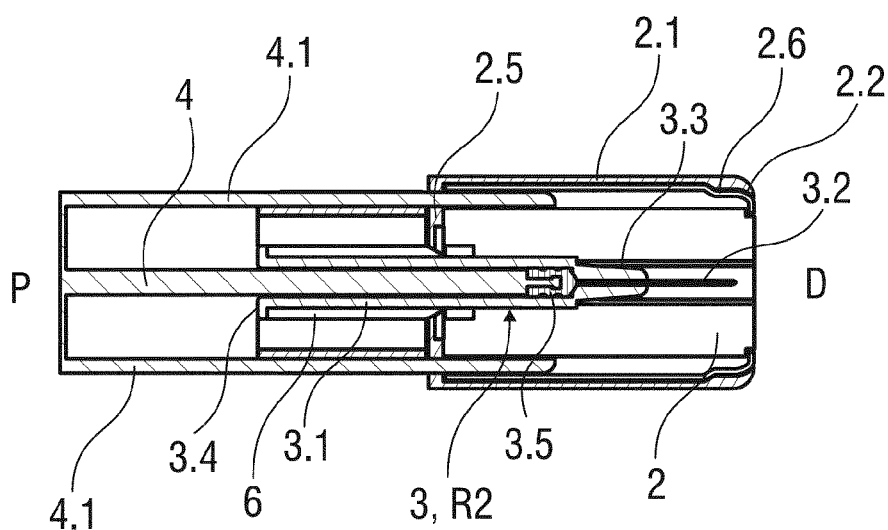
FIG. 6 shows a sectional view of the injection device according to the first embodiment of the invention in retracted and needle safe state.

FIG. 6 shows the injection device 1 in a needle safe state after the completion of the injection. The syringe 3 is retracted into the housing 2 in a second retracted position R2 so as to cover the injection needle 3.2 to minimize the risk of a needle stick injury. As the syringe 3 and the plunger 4 are translated with respect to the housing 2 from the advanced position A in the proximal direction P under the load of the biasing means 6, the guide rails 4.1 disengage the ramps 2.6 so as to allow for an inward movement of the latch arms 2.1. Upon reaching the second retracted position R2, the inward projections 2.5 of the latch arms 2.1 clamp to the barrel 3.1 of the syringe 3 so as to prevent a distal movement of the syringe 3 with respect to the housing 2 and a re-exposure of the injection needle 3.2.

Figure 7A:
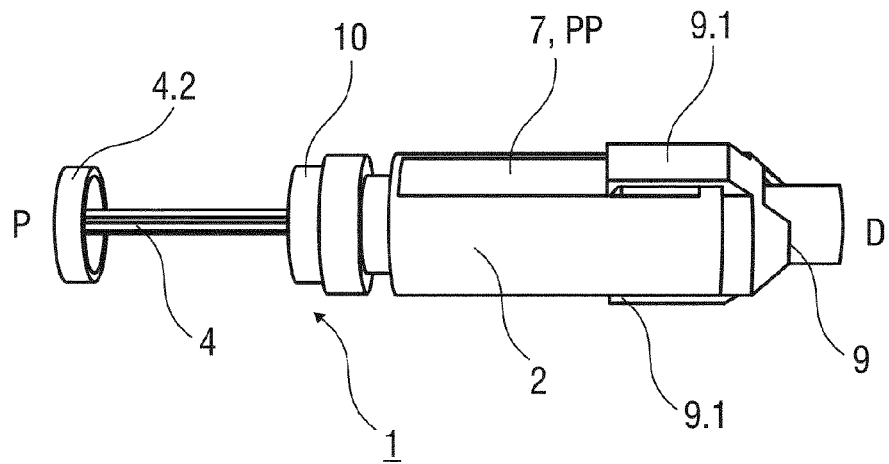
FIG. 7A to 7C show perspective views of an injection device according to a second embodiment of the invention.
Figure 7B:
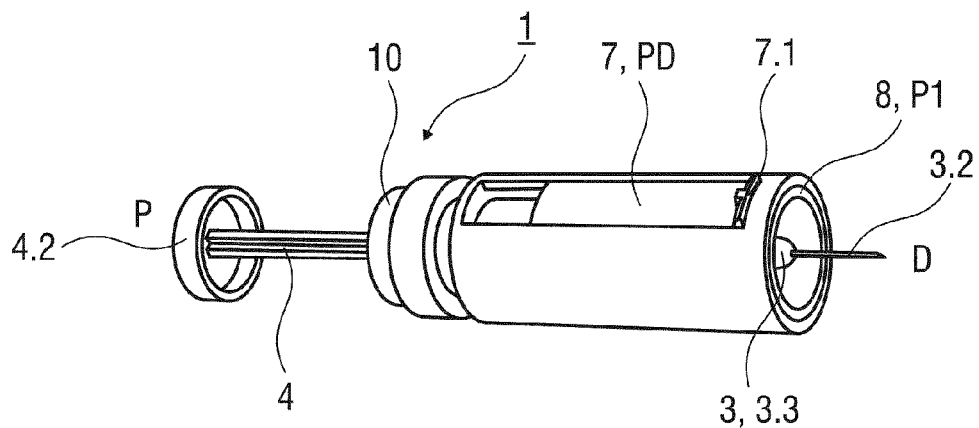
Figure 7C:
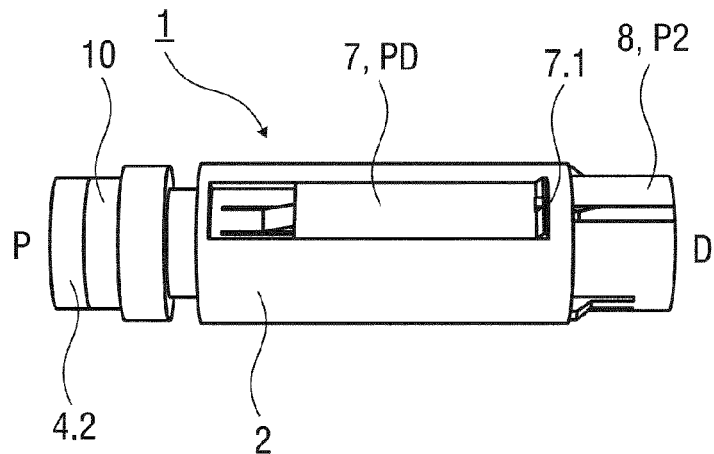

FIGS. 7A to 7C show perspective views of an injection device 1 according to a second embodiment of the invention. A pre-filled syringe 3 with a barrel 3.1 containing a liquid medicament is mounted within a housing 2 of the injection device 1. An activation element 7 is translatably disposed on the housing 2 that may be translated between a proximal position PP and a distal position PD. Movement of the activation element 7 from the proximal position PP to the distal position PD compresses and charges a biasing means 6 disposed within the housing 2 so as to bias a needle shield 8 slidably arranged with respect to the housing in a distal direction D.

The needle shield 8 may slide from a first position P1 and a second position P2. In the first position P1, the needle shield is substantially received within the housing 2 and an injection needle 3.2 of the pre-filled syringe 3 is exposed. In the second position P2, the needle shield 8 projects from the housing 2 in the distal direction D and covers the injection needle 3.2 to provide needle safety after an injection has been carried out.

FIG. 7A shows the injection device 1 according to the second embodiment of the invention in a packaged state as it would presented to an end-user. The activation element 7 is located in the proximal position PP corresponding to the arrangement of the biasing means 6 in an unstressed state so as to minimize material fatigue during transport and storage of the injection device 1.

A cover element 9 covers a distal end of the housing 2 and surrounds the injection needle 3.2 attached to a distal nozzle 3.3 of the pre-filled syringe 3 before use. The cover element 9 may be pulled off the distal end of the injection device 1 to expose the injection needle 3.2. Two clamp arms 9.1 project from opposite sides of the cover element 9 in a proximal direction P. The clamp arms 9.1 are arranged to latch to a proximal ramp 7.1 of the activation element 7. The activation element 7 may thus be translated from the proximal position PP in the distal direction D by pulling off the cover element 9, whereby the biasing means 6 is compressed and charged.

A release element 10 protrudes from the housing 2 in the proximal direction P. The release element 10 is translatably disposed within the housing 2 and may be translated in the distal direction D to release needle shield 8 from being retained in the first position P1 so that the needle shield 8 may be advanced to the second position P2 to cover the injection needle 3.2 after the medicament has been delivered to a patient.

A plunger 4 projects from the housing 2 in the proximal direction P. The plunger 4 is adapted to be depressed into the barrel 3.1 of the pre-filled syringe 3 to expel the medicament contained therein through the injection needle 3.2. The plunger 4 comprises a thumb rest 4.2 that is arranged to abut against the release element 10 at the end of an injection stroke. The release element 10 may thus be pushed in the distal direction D by depressing the plunger 4 into the housing 2 so as to release the needle shield 8 after the medicament has been substantially disposed beneath the skin of the patient receiving the injection.

FIG. 7B shows the injection device 1 according to the second embodiment of the invention in an activated state before drug delivery. The cover element 9 has been removed from the distal end of the injection device 1, whereby the activation element 7 was translated into the distal direction D. The activation element 7 is positioned in the distal position PD and the biasing means 6 disposed within the housing 2 is compressed and energized.

FIG. 7C shows a perspective view of the injection device 1 in a needle safe state after the injection has been completed. The needle shield 8 projects distally from the housing 2 and covers the injection needle 3.2 to prevent accidental needle stick injuries.

Figure 8:
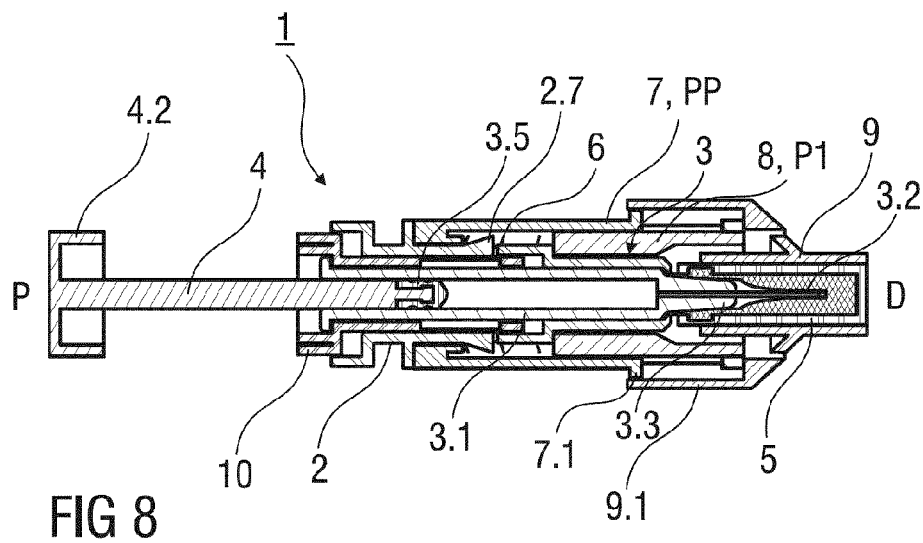
FIG. 8 shows a sectional view of the injection device according to the second embodiment of the invention in a packaged state.

FIG. 8 shows a sectional view of the injection device 1 in the packaged state. The cover element 9 is attached to the distal end of the injection device 1 and comprises a boot 5 that frictionally engages the nozzle 3.3 of the pre-filled syringe 3. The clamp arms 9.1 clamp to the proximal ramp 7.1 of the activation element 7 so that the activation element 7 may be slid from the proximal position PP in the distal direction be pulling off the cover element 9, whereby the biasing means 6 arranged between activation element 7 and the needle shield 8 is compressed and thus charged.

The biasing means 6 of the second embodiment is arranged as a compression spring made from a metal. However, it is foreseen that other suitable arrangements and materials may be used as a biasing means. In particular, the biasing means 6 may be arranged as compressible foam made from a resiliently deformable plastics material.

The housing 2 comprises ramped first protrusions 2.7 that allow for a translation of the activation element 7 from the proximal position PP in the distal direction D. The ramped first protrusions 2.7 project radially outwards from an inner surface of the housing 2 and are adapted to retain the activation element 7 against the load of the charged biasing means 6 in the distal position PD.

A stopper 3.5 connected to the plunger 4 is slidably disposed within the barrel 3.1. The stopper 3.5 fluid tightly seals a proximal end of the barrel 3.1 and is arranged to be translated in the distal direction D by manually depressing the plunger 4 into the barrel 3.1 so as to expel the medicament contained therein through the injection needle 3.2 of the pre-filled syringe 3.

Figure 9:
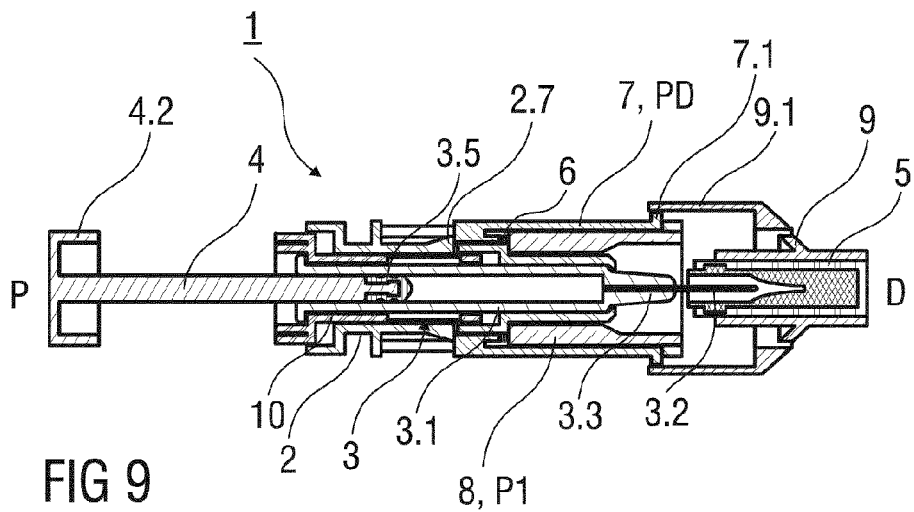
FIG. 9 illustrates energizing of a biasing means of the injection device according to the second embodiment of the invention in a sectional view.

FIG. 9 illustrates the charging of the biasing means 6 of the injection device 1 according to the second embodiment of the invention before drug delivery. The cover element 9 is manually translated in the distal direction D. As the clamp arms 9.1 of the cover element 9 latch to the proximal ramps 7.1 of the activation element 7, the activation element 7 jointly travels in the distal direction D until it reaches the distal position PD. When the activation element 7 is in the distal position PD, the biasing means 6 is full compressed and charged. The first protrusion 2.7 of the housing 2 abuts against the activation element 7 in the distal direction D preventing a proximal movement of the activation element 7 with respect to the housing 2 so as to retain the activation element 7 in the distal position PD against the load of the energized biasing means 6.

Figure 10A:
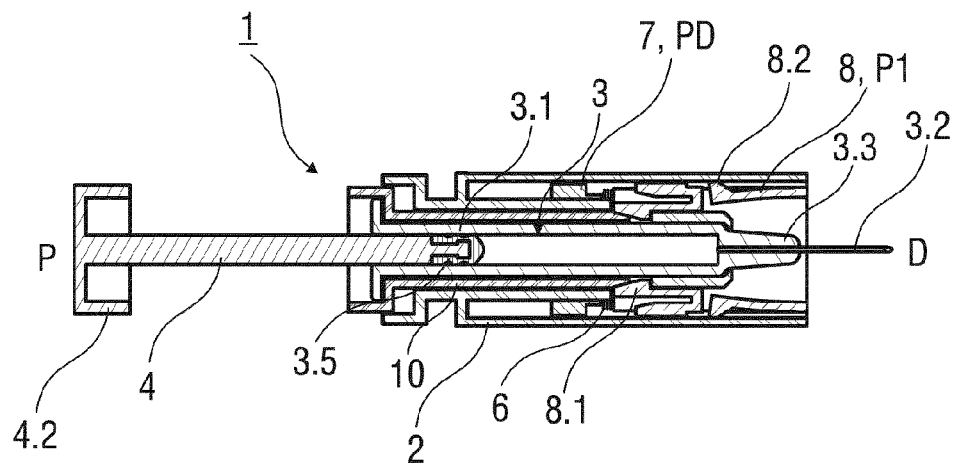
FIGS. 10A and 10B show sectional views of the injection device according to the second embodiment of the invention in before drug delivery.
Figure 10B:
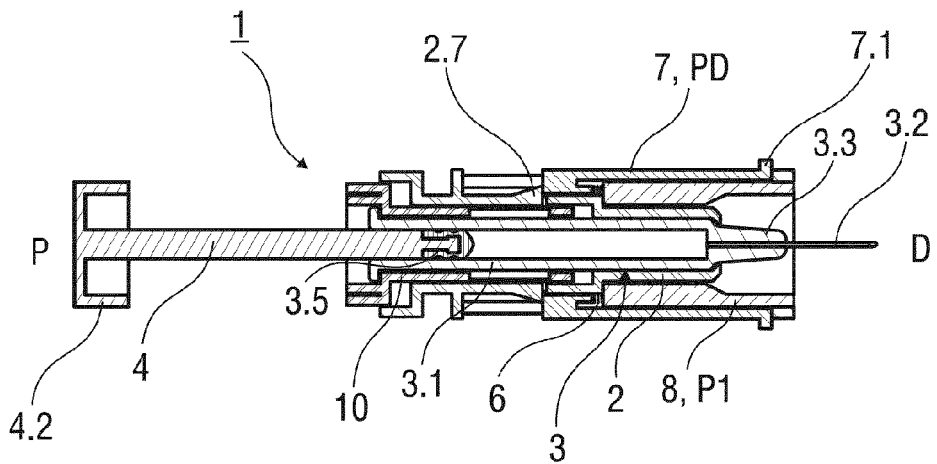

FIGS. 10A and 10B show sectional views of the injection device 1 according to the second embodiment before an injection is performed. The sectional plane shown in FIG. 10A extends perpendicularly to the one shown in FIG. 10B.

The cover element 9 with the boot 5 has been removed and the injection needle 3.2 projects from the housing 2 in the distal direction D. The activation element 7 is retained in the distal position PD and the needle shield 8 is substantially received within the housing 2 in the first position P1. The biasing means 6 arranged between the needle shield 8 and the activation element 7 is in a maximal compressed and stressed state biasing the activation element 7 and the needle shield 8 away from each other. The activation element 7 is retained against the biasing force of the biasing means 6 in the distal position PD by the first protrusion 2.7 abutting against a proximal end of the activation element 7 in the distal direction. A distal displacement of the needle shield 8 with respect to the housing 2 is blocked by first clips 8.1 protruding from the needle shield 8 radial inwards into a corresponding recess formed into the housing 2 so as to retain the needle shield 8 in the first position P1 under the load of the charged biasing means 6.

The needle shield 8 further comprises second clips 8.2 projecting in the radial outward direction. The second clips 8.2 are adapted to latch to the housing 2 of the injection device 1 when the needle shield 8 reaches the second position P2 covering the injection needle 3.2 after the injection so as to block a subsequent proximal movement of the needle shield 8 preventing a re-exposure of the injection needle 3.2.

The release element 7 has the shape of a sleeve that is inserted into the housing 2. A distal end of the release element 7 is arranged to abut against the ramped surface of the first clips 8.1 when translated with respect to the housing 2 in the distal direction D so as to resiliently deflect the first clips 8.1 radially outwards to release the needle shield 8.

Figure 11A:
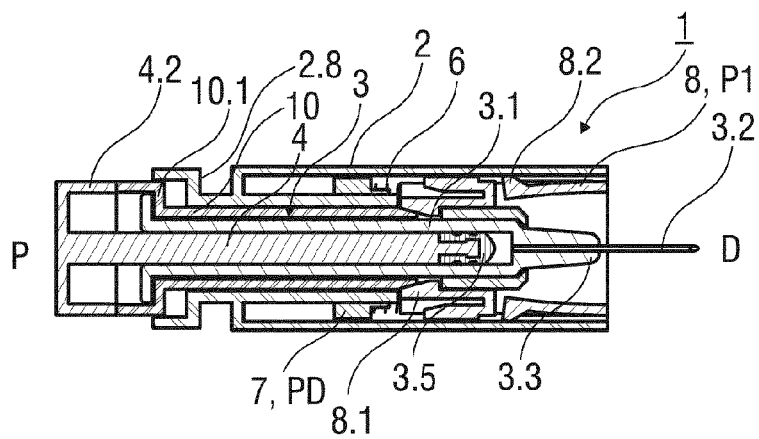
FIGS. 11A and 11B show sectional views of the injection device according to the second embodiment of the invention in after drug delivery.
Figure 11B:
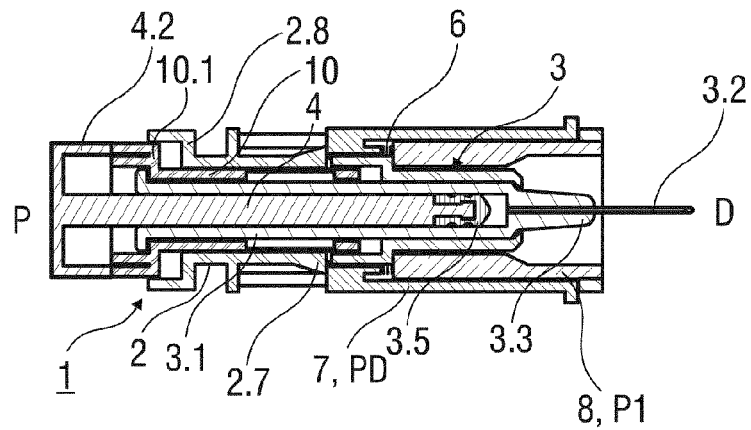

FIGS. 11A and 11B show sectional views of the injection device 1 according to the second embodiment at the end of the drug delivery stage of the injection. The sectional plane shown in FIGS. 11A and 11B respectively correspond to the ones shown in FIGS. 10A and 10B.

The plunger 4 is almost completely depressed into the barrel 3.1 of the pre-filled syringe 3. The stopper 3.5 is located in proximity of a distal end of the barrel 3.1 and most of the medicament has been expelled through the injection needle 3.2. The thumb rest 4.2 abuts distally on the release element 10 so that a further distal movement of the plunger 4 with respect to the housing 2 depresses the release element 10 into the housing 2 to release the first clips 8.1 retaining the needle shield 8 in the first position P1.

The release element 10 comprises an annular first shoulder 10.1 corresponding to a second shoulder 2.8 formed to the housing 2. The release element 10 may be translated with respect to the housing 2 until the first shoulder 10.1 abuts against the second shoulder 2.8 of the housing 2. The distance by which the release element 10 may be translated with respect to the housing 2 in the distal direction D substantially corresponds to the distance of the stopper 3.5 by which the stopper 3.5 is spaced away from the distal end of the barrel 3.1. Thus, the final translation of the plunger 4 with respect to the housing 2 both expels the medicament remaining in the barrel 3.1 through the injection needle 3.2 and pushes the release element 10 against the ramped surface of the first clip 8.1 to release the needle shield 8.

Figure 12A:
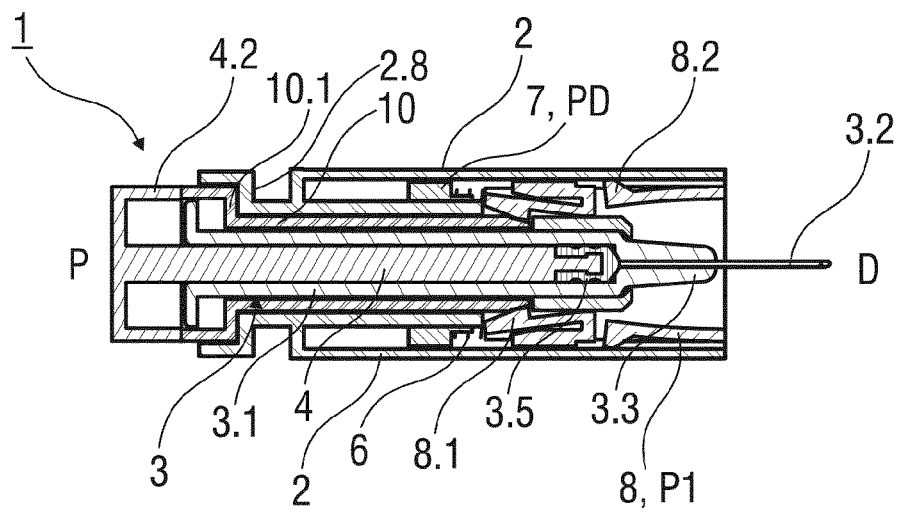
FIGS. 12A and 12B illustrates release of a needle shield of the injection device according to the second embodiment of the invention in sectional views.
Figure 12B:
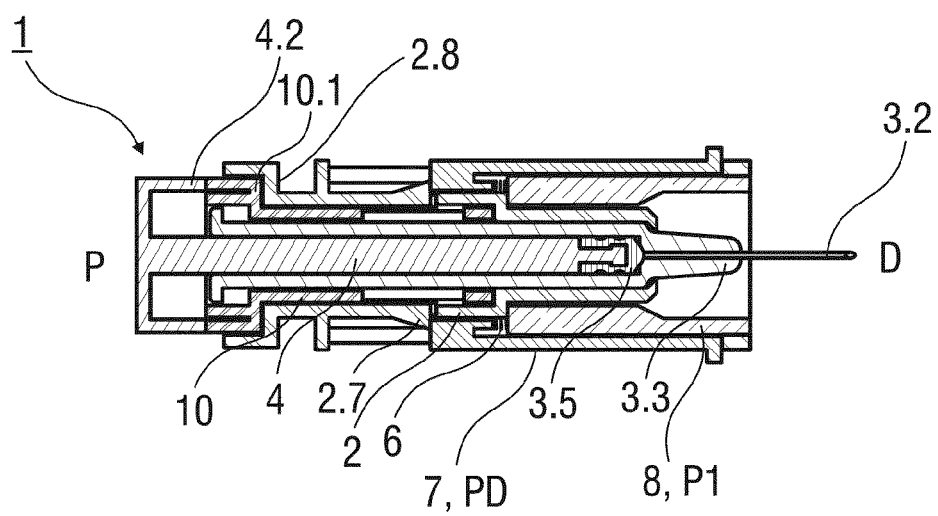

FIGS. 12A and 12B show sectional views of the injection device 1 according to the second embodiment illustrating the release of the needle shield. The sectional plane shown in FIG. 12A extends perpendicularly to the one shown in FIG. 12B.

The plunger 4 is fully depressed into the syringe 3 and the stopper 3.5 has bottomed out in the barrel 3.1. The medicament initially contained in the syringe 3 has been completely disposed beneath the skin of the patient receiving the injection. The release element 10 has been depressed into the housing 2 until the first shoulder 10.1 abuts against the second shoulder 2.8. The distal end of the sleeve-like release element 10 abuts against the ramped surface of the first clips 8.1. The first clips 8.1 are splayed radial outwards to release the needle shield 8 from being retained in the first position P1. The needle shield 8 may now be advanced by the charged biasing means 6 in the distal direction towards the second position P2.

Figure 13A:
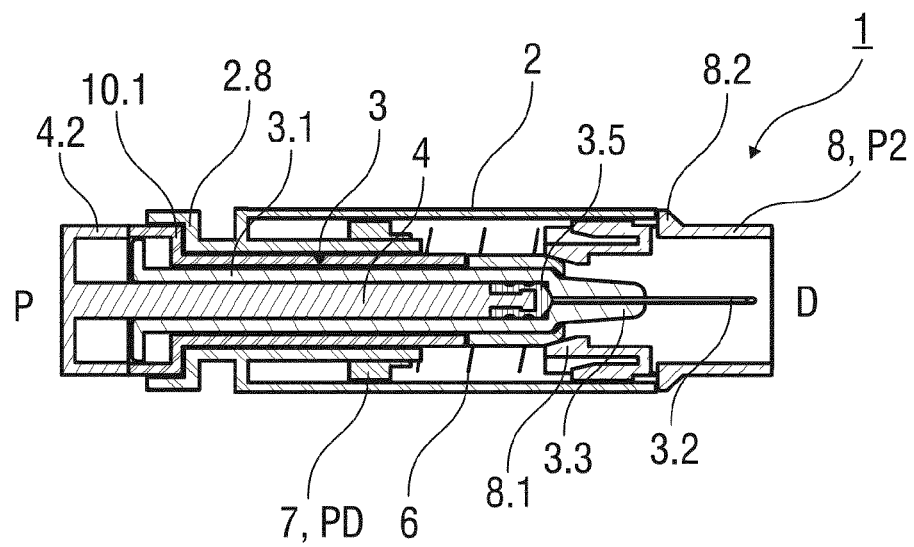
FIGS. 13A and 13B show sectional views of the injection device according to the second embodiment of the invention in a needle safe state.
Figure 13B:
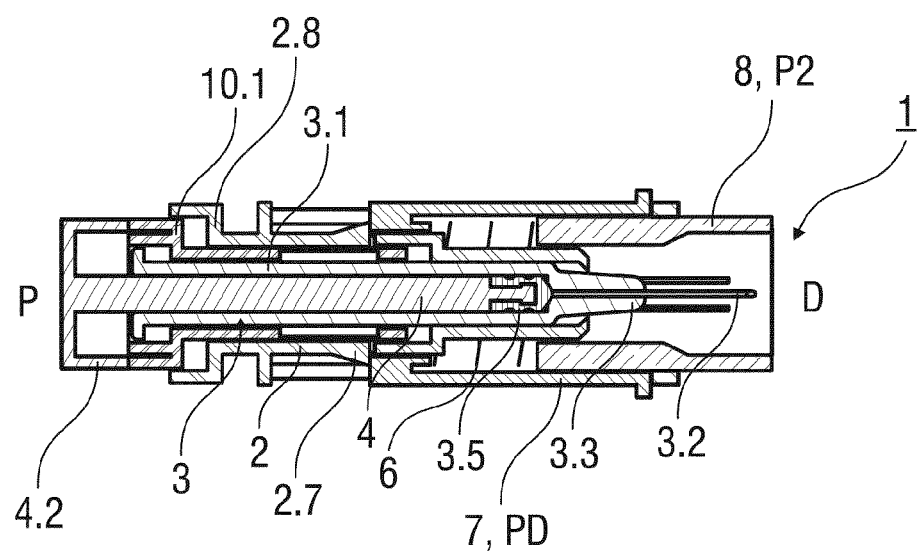

FIGS. 13A and 13B show sectional views of the injection device 1 according to the second embodiment in a needle safe state after the injection is completed. The sectional plane shown in FIG. 13A extends perpendicularly to the one shown in FIG. 13B. The needle shield 8 is in the extended second position P2 and covers the injection needle 3.2 to minimize the risk of an infectious needle stick injury. The second clips 8.2 latch to the distal end of the housing 2 to firmly lock the needle shield 8 to the second position P2 so as to prevent a re-exposure of the injection needle 3.2.

The invention claimed is:

1. An injection device for administering a liquid comprising a pre-filled syringe and a safety mechanism for providing needle safety for an injection needle of the pre-filled syringe, wherein the pre-filled syringe comprises:
  a barrel containing the liquid,
  a stopper translatably disposed within the barrel,
  the injection needle attached to a distal end of the barrel and wherein the safety mechanism comprises
  a substantially cylindrical housing adapted to contain the pre-filled syringe,
  a plunger connectable to the stopper of the pre-filled syringe and adapted to be translated in a distal direction (D) to expel the liquid through the injection needle,
  an energizable biasing member arranged between the housing and the pre-filled syringe, wherein the energized biasing means is capable of biasing the pre-filled syringe with respect to the housing in a proximal direction (P) and
  a retaining mechanism for retaining the pre-filled syringe with respect to the housing in a first retracted position (R1), in an advanced position (A) and in a second retracted position (R2), wherein the injection needle is covered by the housing in the first and second retracted positions (R1, R2) and wherein the injection needle projects distally from the housing in the advanced position,
  wherein the biasing member is arranged in a non-energized state when the pre-filled syringe is in the first retracted position (R1) and wherein the biasing member is adapted to be energized upon translation of the pre-filled syringe from the first retracted position (R1) to the advanced position (A) so as to bias the syringe from the advanced position (A) towards the second retracted position (R2), and wherein a boot is detachably connected to the distal end of the barrel that covers the injection needle before an injection and provides a translation member for manually translating the pre-filled syringe from the first retracted position (R1) to the advanced position (A).

2. The injection device according to claim 1, wherein the retaining mechanism comprises at least one latch arm that is arranged on the housing so as to pivot with respect to the housing about a pivot point to frictionally engage and disengage the barrel or a collar of the syringe.

3. The injection device according to claim 2, wherein the at least one latch arm is arranged to interact with a guide rail of the plunger so as to pivot about the pivot point to release the syringe from being retained in the advanced position (A) when the plunger is substantially depressed into the barrel.

4. The injection device according to claim 1, wherein the energizable biasing member is made from a plastic material.

5. The injection device according to claim 1, wherein the energizable biasing member is made from compressible foam material.

6. An injection device for administering a liquid comprising a pre-filled syringe and a safety mechanism for providing needle safety for an injection needle of the pre-filled syringe, wherein the pre-filled syringe comprises:
  a barrel containing the liquid,
  a stopper translatably disposed within the barrel,
  the injection needle attached to a distal end of the barrel and wherein the safety mechanism comprises
  a substantially cylindrical housing adapted to contain the pre-filled syringe,
  a plunger connectable to the stopper of the pre-filled syringe and adapted to be translated in a distal direction (D) to expel the liquid through the injection needle,
  a needle shield translatably disposed with respect to the housing,
  an energizable biasing member arranged between the housing and the needle shield, wherein the energized biasing member is capable of biasing the needle shield with respect to the housing in the distal direction (D),
  an activation element adapted to be translated with respect to the housing from a proximal position (PP) to a distal position (PD) and
  a retaining mechanism for retaining the needle shield with respect to the housing in a first position (P1) and in a second position (P2), wherein the injection needle projects distally from the needle shield in the first position (P1) and wherein the injection needle is covered by the needle shield in the second position (P2),
  wherein the biasing member is arranged in a non-energized state when the activation element is in the proximal position (PP) and wherein the biasing member is adapted to be energized upon translation of the activation element from the proximal position (PP) to the distal position (PD) so as to bias the needle shield from the first position (P1) towards the second position (P2), and wherein a cover element detachably connected to a distal end of the housing covers the injection needle before an injection and provides a translation member for translating the activation element from the proximal position (PP) to the distal position (PD).

7. The injection device according to claim 6, wherein a boot covering the injection needle is integrated to the cover element.

8. The injection device according to claim 6, wherein the cover element comprises at least one clamp arm adapted to latch to the activation element.

9. The injection device according to claim 6, wherein the housing comprises at least one ramped first protrusion that is arranged so as to allow for a translation of the activation element from the proximal position (PP) to the distal position (PD) and firmly secures the activation element in the distal position (PD).

10. The injection device according to claim 6, wherein the retaining mechanism comprises at least one ramped first clip and at least one second clip arranged on the needle shield and adapted to engage the housing, wherein the first clip is adapted to releasably retain the needle shield in the first position (P1) and the second clip is adapted to firmly retain the needle shield in the second position (P2).

11. The injection device according to claim 10, wherein the retaining mechanism further comprises a release element that is adapted to be translated with respect to the housing in the distal direction (D), wherein the distal translation of the release element engages the ramped surface of the first clip so as to release the needle shield from being retained in the first position (P1).

12. The injection device according to claim 11, wherein the release element projects from the housing in the proximal direction (P) and is adapted to abut against a thumb rest of the plunger when the plunger is substantially depressed into the barrel.

13. The injection device according to claim 11, wherein the release element comprises a first shoulder and the housing comprises a corresponding second shoulder, wherein the first shoulder is arranged to abut against the second shoulder to limit the distal translation of the release element.

* * * * *